(12) United States Patent
Mallet et al.

(10) Patent No.: US 6,632,615 B2
(45) Date of Patent: Oct. 14, 2003

(54) METHOD FOR ISOLATING A TARGET BIOLOGICAL MATERIAL, CAPTURE PHASE, DETECTING PHASE AND REAGENT CONTAINING THEM

(75) Inventors: Francois Mallet, Villeurbanne (FR); Thierry DeLair, Echalas (FR); Catherine Ladaviere, Ste Foy les Lyon (FR); Armelle Novelli-Rousseau, Seyssins (FR); Marie-Helene Charles, Condrieu (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/230,846

(22) PCT Filed: Jun. 19, 1998

(86) PCT No.: PCT/FR98/01299

§ 371 (c)(1),
(2), (4) Date: Apr. 21, 1999

(87) PCT Pub. No.: WO98/59241

PCT Pub. Date: Dec. 30, 1998

(65) Prior Publication Data

US 2002/0192840 A1 Dec. 19, 2002

(51) Int. Cl.⁷ ................. G01N 33/53; A61K 51/00; A61K 49/00; A61K 39/395; C12Q 1/00

(52) U.S. Cl. ................. 435/7.1; 424/1.57; 424/9.1; 424/175.1; 435/4; 435/7.1; 435/7.2; 435/7.8; 435/7.92; 435/7.93; 435/7.94; 435/7.95; 435/69.3; 435/115; 435/345; 436/501; 436/506; 436/512; 436/518; 436/543; 436/544; 530/388.9; 530/389.3; 530/403

(58) Field of Search .................. 424/1.57, 9.1, 424/175.1; 435/7.1, 69.3, 345, 4, 7.2, 7.8, 7.92–7.95, 115; 436/506, 512, 518, 519, 543; 530/388.9, 389.8, 403

(56) References Cited

U.S. PATENT DOCUMENTS 5,439,972 A * 8/1995 Charles et al. ............. 525/54.1
5,489,653 A * 2/1996 Charles et al. ............. 525/327.5

FOREIGN PATENT DOCUMENTS

| EP | 0 319 012 A2 | 6/1989 |
| EP | 0 561 722 A1 | 9/1993 |
| EP | 0 632 269 A1 | 1/1995 |
| WO | WO 96/22533 | 7/1996 |

OTHER PUBLICATIONS

Yang et al. 1986. American Chemical Society, Abstracts of Paper at the National Meeting. p. 13.*
Porath, Jerker et al., "Metal Chelate Affinity Chrromatography, A New Approach to Protein Fractionation," Nature, vol. 258, Dec. 18, 1975, pp. 598–599.
Porath, Jerker, "IMAC–Immobilized Metal Ion Affinity Based Chromatography," Trends in Analytical Chemistry, vol. 7, No. 7, 1988, pp. 254–259.
Cheynet, Valerie et al., "Overexpression of HIV–1 Proteins in *Eschericia coli* by a Modified Expression Vector and Their One–Step Purification," Protein Expression and Purification 4, 1993, pp. 367–372.
Yang, T., et al., "Covalent Immobilization of Immunoglobulin to Polystyrene and Silicon Nitride Chips", American Chemical Society, Abstracts of Paper at the National Meeting, 1986, p. 13.

* cited by examiner

*Primary Examiner*—Mark Navarro
*Assistant Examiner*—Jana Hines
(74) *Attorney, Agent, or Firm*—Oliff & Berridge, PLC

(57) ABSTRACT

The invention concerns a method for isolating a target biological material contained in a sample, which consists in providing a capture phase comprising an organic molecule having at least a reactive function and at least a protein material capable of recognizing or binding, specifically and directly or indirectly, with the target biological material, said protein material having a specific covalent binding site with the organic molecule reactive function, consisting of at least a tag comprising at least six contiguous lysine, or lysine derivative residues, the method consists in contacting said target biological material with at least the capture phase; and detecting the target biological material fixed on the capture phase: The invention also concerns the capture and detection phases, and a reagent containing them.

36 Claims, 5 Drawing Sheets

SEQUENCE LISTING

```
<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: Oligonucleotide used to prepare synthetic
      adaptor

<400> SEQUENCE: 1
gggaagaaga agaagaagaa gtctgtcgac gaatctct                             38

<210> SEQ ID NO 2
<211> LENGTH: 42
<212> TYPE: DNA
<213> ORGANISM: Artificial Sequence
<220> FEATURE:
<223> OTHER INFORMATION: Oligonucleotide used to prepare synthetic
      adaptor

<400> SEQUENCE: 2
ctagagagat tcgtcgacag acttcttctt cttcttcttc cc                        42

<210> SEQ ID NO 3
<211> LENGTH: 46
<212> TYPE: DNA
<213> ORGANISM: Artificial Sequence
<220> FEATURE:
<223> OTHER INFORMATION: C-terminal of adaptor
<220> FEATURE:
<221> NAME/KEY: CDS
<222> LOCATION: (1)..(45)
```

```
<400> SEQUENCE: 3 ccc ggg aag aag aag aag aag tct gtc gac gaa tct ctc tag a     46
Pro Gly Lys Lys Lys Lys Lys Ser Val Asp Glu Ser Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: C-terminal of adaptor

<400> SEQUENCE: 4

Pro Gly Lys Lys Lys Lys Lys Ser Val Asp Glu Ser Leu
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Polyhistidine tag

<400> SEQUENCE: 5

Met Arg Gly Ser His His His His His His Gly Ser Val Asp Glu Ser
1               5                   10                  15

Met

<210> SEQ ID NO 6
<211> LENGTH: 23
<212> TYPE: PRT
<213> ORGANISM: Artificial Sequence
<220> FEATURE:
<223> OTHER INFORMATION: Polylysine tag

<400> SEQUENCE: 6

Met Arg Gly Ser Cys His Lys Lys His His Lys Lys His His Lys Lys
1               5                   10                  15

Gly Ser Val Asp Glu Ser Met
            20

<210> SEQ ID NO 7
<211> LENGTH: 12
<212> TYPE: PRT
<213> ORGANISM: Artificial Sequence
<220> FEATURE:
<223> OTHER INFORMATION: Polylysine tag

<400> SEQUENCE: 7

Lys Lys Lys Lys Lys Lys Ser Val Asp Glu Ser Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Polylysine tag

<400> SEQUENCE: 8

Cys Lys Lys Lys Lys Lys Lys Ser Val Asp Glu Ser Leu
1               5                   10
```

METHOD FOR ISOLATING A TARGET BIOLOGICAL MATERIAL, CAPTURE PHASE, DETECTING PHASE AND REAGENT CONTAINING THEM

The invention relates to a method for isolating a target biological material contained in a sample, using a capture phase comprising an organic molecule containing at least one reactive function, and at least one protein material capable of recognizing or binding, specifically and directly or indirectly, to the target biological material, said protein material containing a specific site for covalently binding to the reactive function of the organic molecule.

A method for immobilizing a protein on a solid support, by means of reactive functions, in order to stimulate the proliferation or growth of T cells and the production of killer lymphocytes is known from document EP-A-0,319,012. To this end, the protein has, at its C-terminal end, a covalent-binding site for binding to said reactive functions, which consists of an amino acid sequence in which are distributed two to four lysine residues.

The problem posed by the covalent-binding site of this prior art lies in the fact that, in a diagnostic application, the results of the isolation of a target biological material with which it is capable of binding are similar to those obtained with a protein material which does not contain such a binding site.

According to the invention, a method is provided for isolating a target biological material by using at least one capture phase which comprises a protein material containing a covalent-binding site which allows efficient orientation of said protein material, and leads to sensitive, high-quality detection of said biological material.

Thus, the method of the invention, for isolating a target biological material contained in a sample, comprises the following steps:
  a capture phase is provided, which comprises an organic molecule containing at least one reactive function and at least one protein material capable of recognizing or binding, specifically and directly or indirectly, to the target biological material, said protein material containing a specific site for covalent binding to the reactive function of the organic molecule, which consists of at least one tag comprising at least six contiguous lysine or lysine-based residues,
  said target biological material is placed in contact with at least one capture phase, and
  the target biological material bound to the capture phase is detected.

According to the invention, the expression "isolating a biological material" means the binding, separation, isolation, detection and/or quantification of this material, the enrichment of a fraction with target biological material, according to a qualitative and/or quantitative, specific or aspecific binding method.

According to one variant of the method, the capture phase can also comprise a label, and, in this case in particular, it can consist of a detection phase.

According to another variant of the method, a detection phase is also provided, which comprises an organic molecule containing at least one reactive function, at least one protein material capable of recognizing or binding, specifically and directly or indirectly, to said target biological material, and a label, said protein material containing a specific site for covalent binding to the reactive function of the organic molecule, which consists of at least one tag comprising at least six contiguous lysine or lysine-based residues.

In this case, the organic molecules in the capture phase and in the detection phase, respectively, can be identical or different, and the protein materials in the capture phase and in the detection phase, respectively, can be identical or different.

As is understood by the invention, a sample comprises any sample capable of containing a biological material, in particular a sample such as that obtained from—a biological fluid, a sample of food origin, or a cell culture.

The sample consists of all or part of another sample: in particular it can consist of an aliquot or a dilution.

A protein material according to the invention comprises proteins, in particular recombinant proteins, especially antigens, antibodies and peptides such as synthetic peptides. The method of the invention may also be carried out with a material such as peptide analogues of nucleic acids (PNA).

The term "organic molecule" means a molecule of variable size; thus, this refers equally to a small molecule such as a hapten and to a macromolecule such as a polymer.

As examples of haptens, mention may be made of a hormone, a vitamin, such as biotin, or a medicinal product. In this case, the method of the invention can comprise, before the step of detecting the target biological material, a step of binding the organic molecule to a carrier molecule. Preferably, the hapten is biotin and the carrier molecule is avidin.

A polymer as used according to the invention is a polymer in particulate or in linear form. It can be a homopolymer chosen in particular from polylysine and polytyrosine, or a copolymer chosen in particular from maleic anhydride copolymers, N-vinylpyrrolidone copolymers, natural or synthetic polysaccharides, polynucleotides and amino acid copolymers such as enzymes. Advantageously, it is a copolymer chosen from maleic anhydride/methyl vinyl ether copolymer, N-vinylpyrrolidone/N-acryloxysuccinimide copolymer, poly-6-aminoglucose, and enzymes such as horseradish peroxidase (HRP) or alkaline phosphatase or derivatives thereof bearing at least one reactive function.

The expression "reactive function of the organic molecule" means either a reactive function chosen in particular from ester, halocarbonyl, sulfhydryl, disulfide, epoxide, haloalkyl and aldehyde functions; or a function which can be activated by an activating agent such as carbodiimides or homo- or heterobifunctional compounds. By way of example, an activatable function is chosen in particular from acid, amine and hydroxyl functions.

The covalent-binding sites defined above can exist naturally in the protein material. Alternatively, they can be "incorporated" beforehand into the protein material, in the form of a tag, according to techniques which are well known to those skilled in the art, such as the technique used to purify proteins by the IMAC (immobilized metal ion-affinity chromatography) method on resins (1, 2). By way of example, such sites can be incorporated into a protein material, and in particular a protein, by genetic engineering in order to obtain recombinant proteins.

A tag can be defined as an amino acid sequence which is incorporated into, i.e. added to, the original structure of the protein material, which is introduced into a preferred place in said original structure in order to allow it to be exposed in a relevant manner, in particular with regard to its covalent binding to the organic molecule.

In accordance with the invention, a covalent-binding site of the protein material considered can consist of a tag comprising six or more lysine or lysine-based residues, and optionally other amino acids, or can consist of several of said tags.

The term "lysine-based" means that the lysine can be chemically modified, provided that these modifications essentially preserve or even enhance the specificity of the covalent-binding site. Examples which may be mentioned are the replacement of L-lysine with D-lysine, and vice-versa; a modification of the lysine side chain, such as an acetylation of the amine function or an esterification of the carboxyl function; a modification of the peptide bonds such as, for example, carba, retro, inverso, retro-inverso, reduced and methylenoxy bonds.

The tag(s) described above can be found in any place in the primary structure of the protein material. Preferably, it is located at the N- or C-terminal end of the protein material.

According to the present invention, various methodes are also defined for isolating a target biological material contained in a sample, depending, in particular, on its nature:

- if the target biological material is an antibody, the protein material comprises an antigen which specifically recognizes said antigen;
- if the target biological material is an antigen, the protein material comprises an antibody which specifically recognizes said antigen.

Other subjects of the invention are outlined below.

Thus, the invention relates to a phase for capturing a target biological material which comprises an organic molecule containing at least one reactive function and at least one protein material capable of recognizing or binding, specifically and directly or indirectly, to the target biological material, said protein material containing a specific site for covalent binding to the reactive function of the organic molecule, which consists of at least one tag comprising at least six contiguous lysine residues; preferably, the organic molecule is a polymer or a hapten.

An advantageous polymer is particulate or linear and chosen in particular from homopolymers such as polylysine or polytyrosine; and copolymers such as maleic anhydride copolymers, N-vinylpyrrolidone copolymers, natural or synthetic polysaccharides, polynucleotides and amino acid copolymers such as enzymes. Even more advantageously, the polymer is chosen from maleic anhydride/methyl vinyl ether copolymer, N-vinylpyrrolidone/N-acryloxysuccinimide copolymer, poly-6-aminoglucose, horseradish peroxidase (HRP) and alkaline phosphatase.

If the organic molecule is a hapten, the capture phase can also comprise a suitable carrier molecule. Preferably, the hapten is biotin and, if necessary, the carrier molecule is avidin.

Advantageously, the tag as defined above is placed at the N- or C-terminal end of the protein material.

The reactive function of the organic molecule is chosen in particular from ester, acid, halocarbonyl, sulfhydryl, disulfide, epoxide, haloalkyl and aldehyde functions.

The invention also relates to a phase for detecting a target biological material, having the same characteristics as the above capture phase and also comprising a label.

As indicated above, the organic molecule can be a polymer or a hapten. According to the second possibility, the organic molecule consisting of the hapten also represents the label.

The label for the detection phase is preferably chosen from the group consisting of an enzyme, a protein, a peptide, an antibody, a hapten such as biotin or iminobiotin, a fluorescent compound such as rhodamine, a radioactive compound, a chemiluminescent compound, an electron-density component, a magnetic component and the like.

Another subject of the invention is a reagent for isolating a target biological material, comprising a capture phase of the invention and/or a detection phase of the invention.

Advantageously, the capture phase is bound, directly or indirectly, to a solid support, by passive absorption or by covalency.

The solid support can be in any suitable form, such as a plate, a cone, a bead which is optionally radioactive and/or fluorescent and/or magnetic and/or conductive, a bar, a tube of glass, a well, a sheet, a chip or the like. It is chosen from among polystyrenes, styrene/butadiene copolymers, styrene/butadiene copolymers mixed with polystyrenes, polypropylenes, polycarbonates, polystyrene/acrylonitrile copolymers, styrene/methyl methylmethacrylate copolymers, from among synthetic and natural fibres, and from among polysaccharides and cellulose derivatives, glass, silicon and derivatives thereof.

As will be demonstrated in the experimental section below, the Authors have obtained monoclonal antibodies directed against the tags as defined above and in particular against the tag which consists of a sequence of six lysine residues.

It is thus possible to envisage the use of such a tag in a method for isolating a biological material, according to which:

a capture phase is provided, said target biological material is placed in contact with at least the capture phase, and the target biological material bound to the capture phase is detected, according to which method the capture phase comprises an organic molecule which comprises or consists of an anti-tag antibody and at least one protein material capable of recognizing or of binding, specifically and directly or indirectly, to the target biological material, said protein material containing a specific site for binding to the organic molecule, which consists of at least one tag comprising at least six contiguous lysine or lysine-based residues.

Such a method can also comprise the use of a detection phase, which has the characteristics of the capture phase as has just been described, and also comprising a label. This label can advantageously consist of a said antibody.

The characteristics and advantages of the various subjects of the invention are illustrated below, in support of Examples 1 to 6 and FIGS. 1 to 7.

FIG. 1 represents a graph reflecting the yield of coupling by covalent binding between the protein RH24K (light-shaded bars) and the protein RH24 (dark-shaded bars) and the copolymer, for different coupling conditions; Acet=acetate; Phos=phosphate; Bor=borate; Carb=carbonate.

EXAMPLE 1

Figure 1:
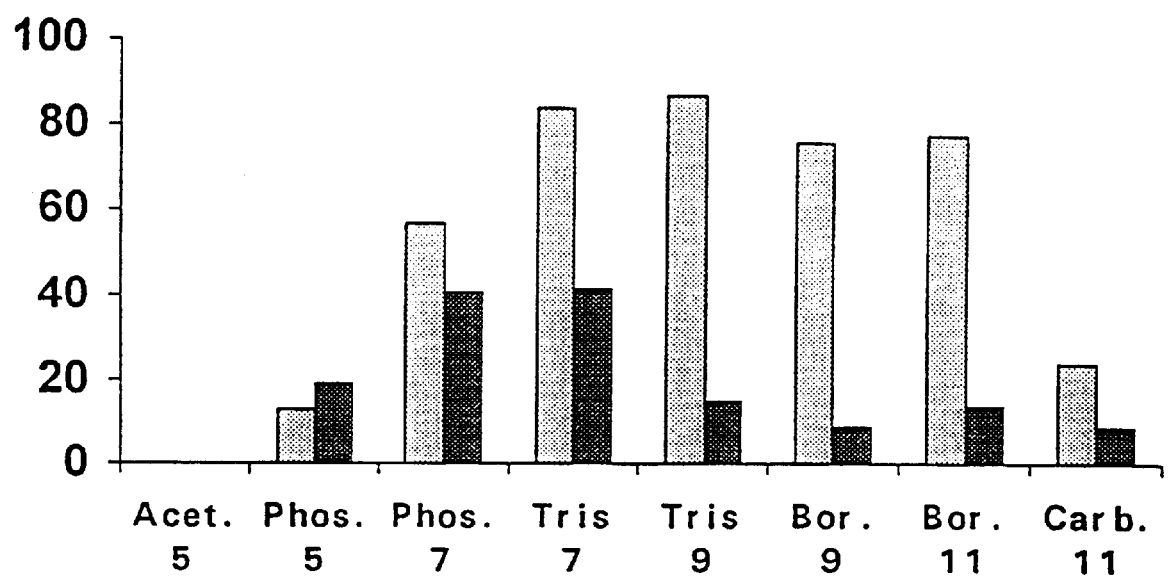

Expression and Purification of RH24K pMH24 (Cheynet et al., 1993) was modified by insertion of a synthetic adapter at the 3' end of the p24 gene in order to express RH24K, corresponding to RH24 which has at its C-terminal end a specific site for covalent binding referred to as a "polylysine tail" and consisting of 6 contiguous lysine residues.

The adapter was prepared beforehand by hybridization of two oligonucleotides having the following respective sequences:
SEQ ID NO: 1: 5' GGGAAGAAGA AGAAGAAGAA GTCTGTCGAC GAATCTCT 3'
SEQ ID NO: 2: 5' CTAGAGAGAT TCGTCGACAG ACT-TCTTCTT CTTCTTCTTCC C 3'
in 10 mM Tris, 50 mM NaCl, 1 mM DTE, 10 mM MgCl$_2$, pH 7.5 buffer, by heating at 70° C. for 5 minutes followed by slow cooling first to 37° C. over 30 minutes and then to room temperature over 30 minutes. This adapter was then cloned between the sites SmaI and XbaI of pMH24 at the 3' end of the RH24 gene. The resultant plasmid, pMH24K3', was amplified in the *E. coli* XLI bacterial strain (recA1, endA1, gyrA96, thi-1, hsdR17, supE44, relA1, lac [F' proAB, lacIPZΔAM15, Tn10 (tet$^r$)] and then sequenced by the Taq Dye Deoxy Terminator Matrix Standart method (Applied Biosystems). The sequence obtained and the corresponding sequence on the protein obtained at the C-terminal are given below.

```
         SmaI
5'ATG                    CCC GGG AAG AAG AAG AAG AAG AAG
Nter Met . . . [247 amino acids] . . . Pro Gly Lys Lys Lys Lys Lys Lys
         XbaI
TCT GTC GAC GAA TCT CTC TAG A 3' (SEQ ID NO: 3)
Ser Val Asp Glu Ser Leu       Cter (SEQ ID NO: 4)
```

The protein is expressed under the control of the Tac promoter in the *E. coli* XLI bacterial strain (see above). A preculture of *E. coli* XLI containing the expression vector, is prepared beforehand overnight at 37° C. in Luria broth (LB) in the presence of ampicillin (amp; 50 μg/ml) and tetracycline (tet; 12 μg/ml) in order to inoculate the LB-amp-tet medium (1/40 to 1/25); this medium is cultured until an OD at 600 nm of 0.6 is obtained. Expression of the protein is then induced by addition of isopropyl-β-D-thiogalactopyranoside (IPTG) to the medium at a concentration of 1 mM for 2h30 at 37° C. with stirring. After centrifugation at 5000 revolutions/min (JA21 rotor, Beckman) for 10 minutes at 4° C., the bacteria are taken up in a 50 mM Tris-HCl, 1 mM EDTA, 100 mM NaCl, 10 mM MgC12, pH 8 buffer (3 ml/g of biomass) in the presence of protease inhibitor (2 μg/ml aprotinine and 2 μg/ml leupeptine) and then lyzed by sonication at 0C. The soluble fraction is taken up by centrifugation at 10,000 revolutions/min (JA21 rotor, Beckman) for 15 minutes at 4° C. and then deposited on a metal-chelating affinity column in order to purify the RH24K (Chelating Sepharose Fast Flow No. 17057501). The gel was preloaded with Zn$^{2+}$ according to the suppliers' recommendations and then equilibrated with a sodium phosphate buffer containing 67 mM NaCl, pH 7.8, and then 200 mM ammonium acetate, 0.5 M NaCl, pH 6. The RH24K is eluted with 200 mM ammonium acetate 0.5 M NaCl pH 4. The fractions collected are dialyzed against 50 mM, pH 7.8 sodium phosphate buffer.

The purified protein is characterized by electrophoresis on SDS-PAGE and by passage in gel filtration/HPLC. Its purity is greater than 90% and thus comparable with the purity of RH24. When analyzed by mass spectrometry, its molecular weight is 28,027, which is compatible with the theoretical molecular weight 27,992. The protein is recognized by polyclonal and monoclonal anti-p24 antibodies in Western Blot and in ELISA.

EXAMPLE 2

Coupling of RH24K and of RH24 to the NAVE Copolymer

5 μl of polymer solution at a concentration of 1 g/l is added to a solution of protein in a suitable buffer, at a concentration of 1 g/l.

The reaction medium is stirred for 3 hours at 37° C.

The reaction progress is monitored by HPLC, on a Waters steric exclusion column with a 0.1 M, pH 6.8 phosphate buffer as mobile phase.

The coupling yields reported in FIG. 1 show that the modified protein couples preferably to the polymer and over a wider spectrum of experimental conditions.

EXAMPLE 3

Effect of the Nature of the Polymer on the Coupling Yield

The effect of the nature of the comonomer forming part of the composition of the polymer is evaluated under the same conditions as those described above.

The results are given in the table below.

TABLE

| Polymer | Coupling yield (%) |
|---|---|
| MAVE poly(methyl vinyl ether/maleic anhydride | 65 |
| PEMA poly (ethylene/maleic anhydride) | 86 |
| SMA poly (styrene/maleic anhydride) | 49 |
| NVPMA poly (N-vinylpyrrolidone/ maleic anhydride | 36 |

The effect of the comonomer is quite pronounced since the coupling yields vary within a range between 36 and 86% depending on the nature of the comonomer.

EXAMPLE 4

Figure 2:
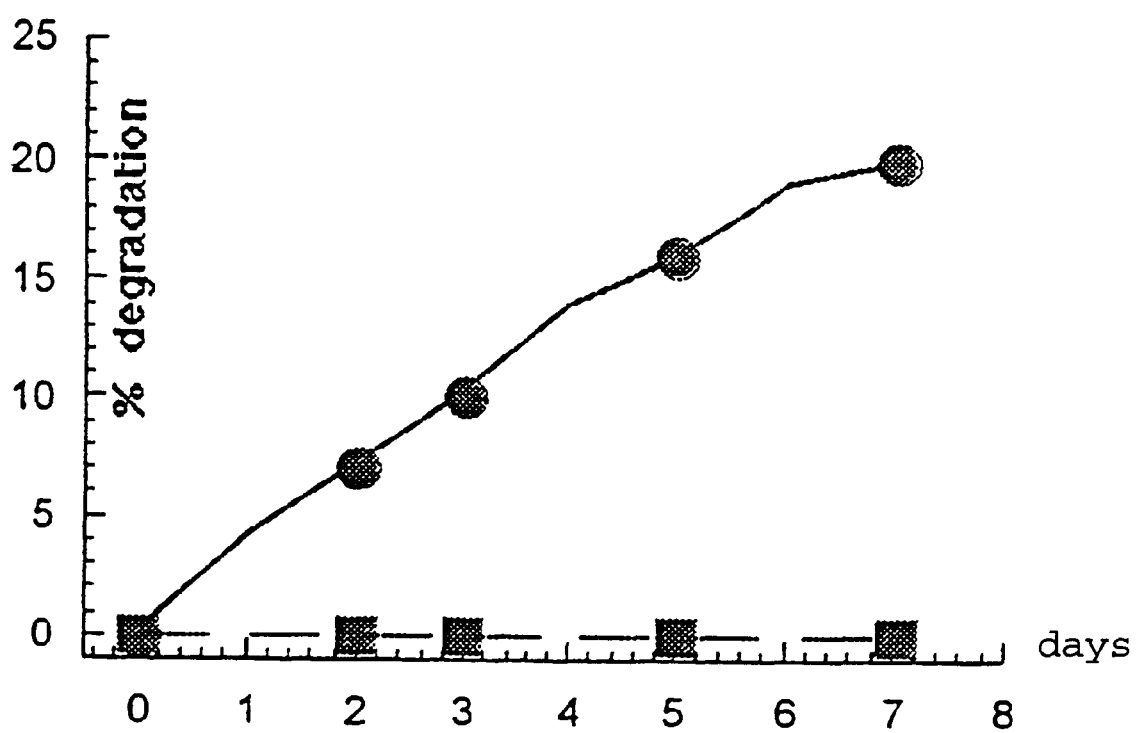
FIG. 2 represents a graph of comparison between the stability as a function of time (in days) of the polymer (MAVE)/protein (RH24K) conjugate compound (curve ■) and that of the free RH24K protein (curve ●).

Compared Stability of the Protein/Polymer Conjugate Compounds with Respect to the Protein Alone The conjugate compounds were stored at 37° C. in the coupling medium and analyzed by steric exclusion chromatography in order to evaluate the amount of residual protein in the coupling medium. The results are given in the graph represented in FIG. 2.

The coupling on polymer thus gives the protein better stability on storage.

EXAMPLE 5

Directed Biotinylation of RH24K

Figure 3:
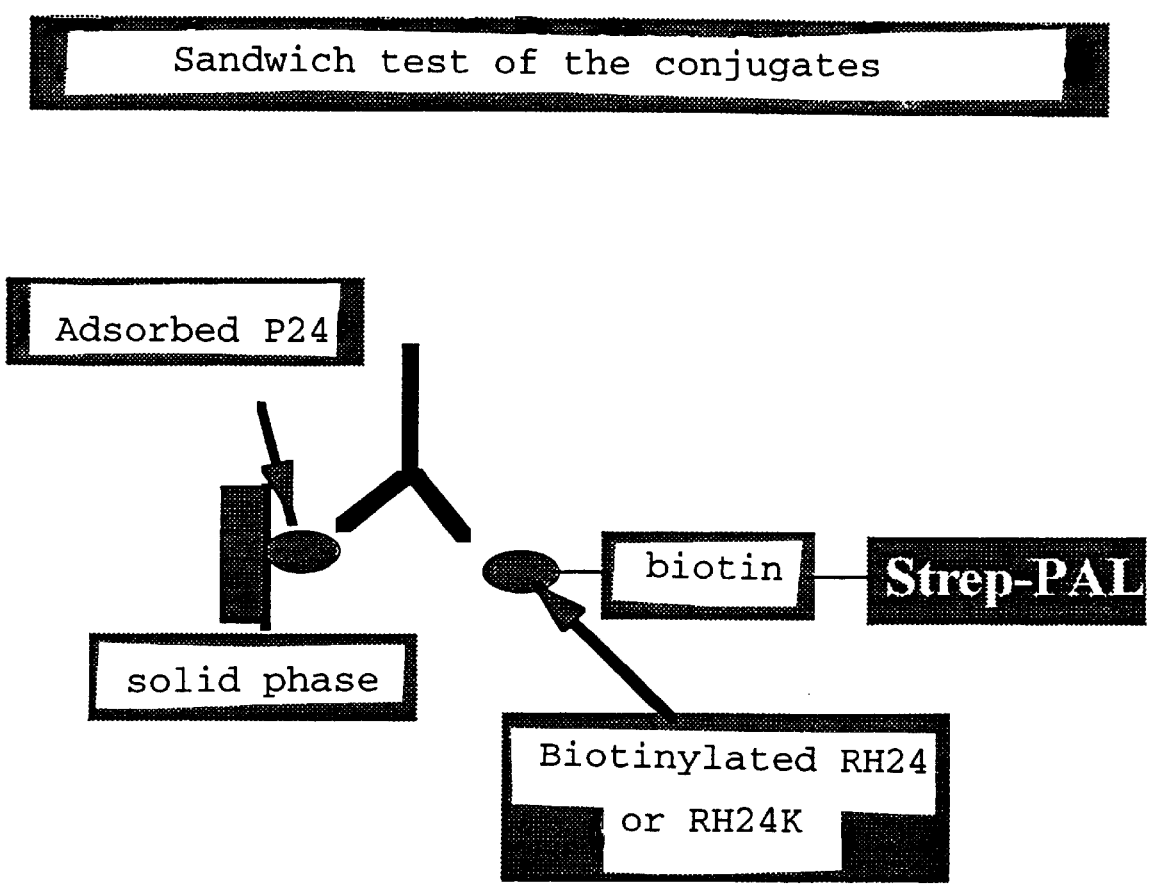
FIG. 3 represents a scheme summarizing the "sandwich" detection technique.

The conjugate compounds prepared are biotinylated p24s (RH24 or RH24K) which will be used in detection in the p24 antigen sandwich test, in accordance with the scheme represented in FIG. 3.

The biotin couplings are carried out on RH24K and on RH24, checked and then analyzed in the antigen sandwich test in order to define the coupling conditions which are favorable to RH24K.

The proteins are used at a concentration of 1 mg/ml. Different buffers were tested on the basis of the buffers tested during the p24/MAVE couplings: 0.1 M borate pH 9.2, 0.1 M Tris pH 7.2, 0.1 M phosphate pH 7.2 and 0.1 M carbonate pH 8.5. The following biotin/p24 ratios were tested: 5/1, 10/1, 25/1, 50/1, 100/1. The couplings were incubated for 1 hour at 37° C.

The p24/biotin conjugate compounds were used in detection according to the schema represented in FIG. 3 with monoclonal antibodies and a positive serum.

Figure 4:
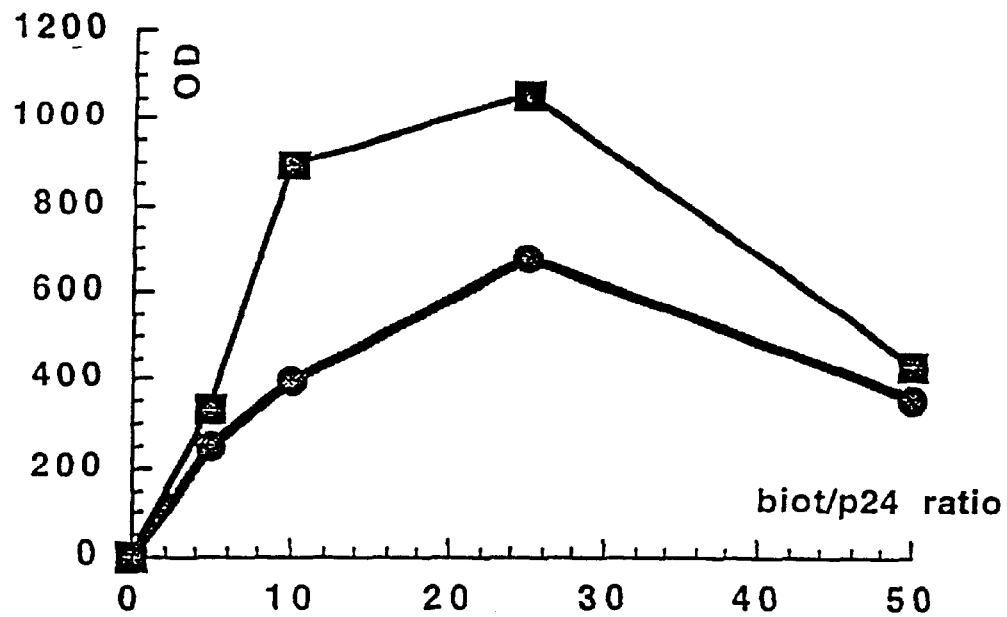
FIG. 4 represents a graph reflecting the immunoreactivity of the polymer/RH24 conjugate compounds (curve ●), and polymer/RH24K conjugate compounds (curve ■), with respect to a monoclonal antibody.
Figure 5:
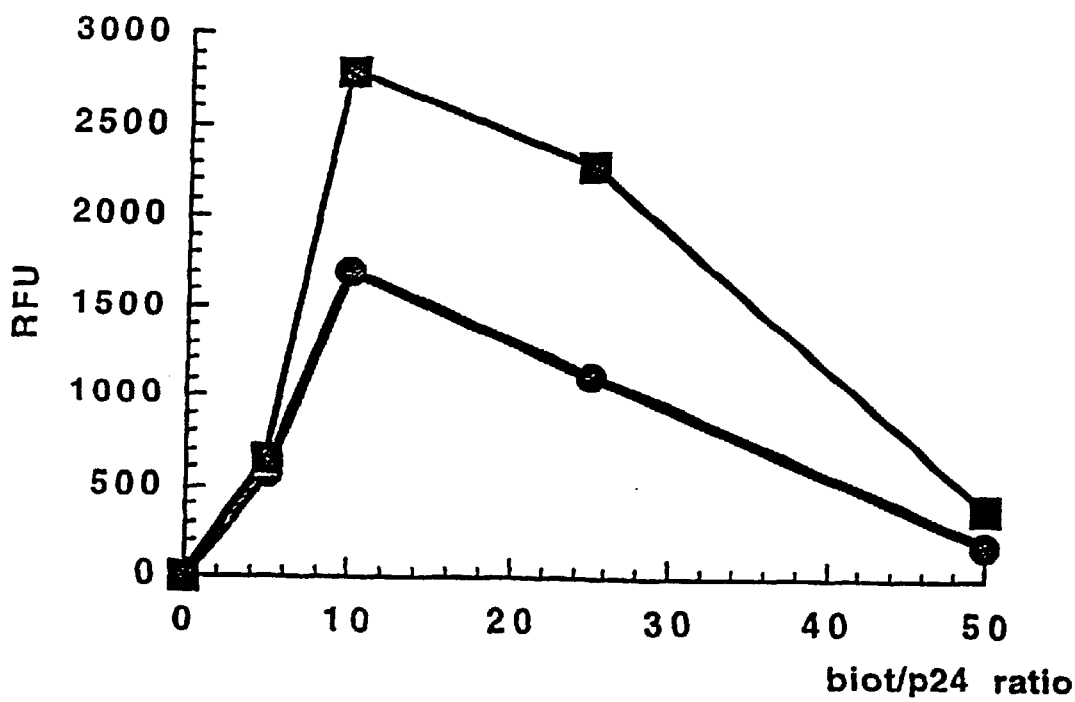
FIG. 5 represents a graph reflecting the immunoreactivity of the polymer/RH24 conjugate compounds (curve ●) and polymer/RH24K conjugate compounds (curve ■), with respect to serum.

The RH24/biotin and RH24K/biotin conjugate compounds show activity in the antigen sandwich test with the monoclonal antibodies and the positive serum. By way of illustration, FIGS. 4 and 5 show, in graph form, the compared responses of the conjugate compounds obtained with RH24K and RH24 at different degrees of biotin functionalization. FIG. 4 relates to the results obtained with a monoclonal antibody, the test being performed on a microtitration plate. FIG. 5 represents the results obtained on serum with the Vidas immunoanalysis automated machine from BioMérieux.

RH24K gives a bigger signal than RH24, irrespective of the experimental conditions tested. An optimum biotin/p24 ratio of 25/1 for the monoclonal antibodies, and of 10/1 for the serum, is observed.

EXAMPLE 6

Influence of the Composition, in Terms of Lysine Residues of the Polylysine Tag, on the Coupling Efficacy The biological material used to evaluate the influence of the composition as lysine residues of the polylysine tag on the coupling efficacy is as follows:

the recombinant protein RH24K; this contains, in its amino-terminal part, a tag [MRGS(H)$_6$GSVDESM] (SEQ ID NO: 5), which serves to purify it by elation with a metal ion, and, in its carboxy-terminal part, a polylysine tag [PG(K)$_6$SVDESL] (SEQ ID NO: 4) dedicated to the coupling; this protein can be represented as follows:

MRGS(H)$_6$GSVDESM-p24-PG(K)$_6$SVDESL)

the recombinant protein RHK24; this contains, in its amino-terminal part, a polylysine tag [MRGSCH(K)$_2$HH(K)$_2$HH(K)$_2$GSVDESM] (SEQ ID NO: 6); this protein can be represented as follows:

MRGSCH(K)$_2$HH(K)$_2$HH(K)$_2$GSVDESM-p24 the recombinant protein R24; this contains neither the carboxy-terminal polylysine tag nor the amino-terminal polyhistidine tag; it can be represented by p24.

The polymers used are MAVE (maleic anhydride co-methyl vinyl ether). The coupling conditions are identical for the three proteins.

Two coupling buffers were used, the 0.1 M, pH 8.2 carbonate buffer and the 0.05 M, pH 9.0 Tris HCl buffer.

The results are given in the following table illustrating the yield for coupling the recombinant proteins with the MAVE polymer carried out under two different reaction conditions. They show the importance of the contiguity of the lysine residues.

The reason for this is that the coupling yield obtained with the protein RH24K (6 contiguous lysine residues) is very much greater than the coupling yield obtained with protein RHK24 (6 lysine residues in three blocks of 2).

In point of fact, the coupling yield obtained with the protein RHK24 (6 lysine residues in three blocks of 2) is similar to that obtained with the protein R24 (no tag).

TABLE

| Protein polylysine tag | R24 no tag | RH24K PG (K)$_6$ SVDESL | RHK24 MRGSCH (K)$_2$HH (K)$_2$ HH (K)$_2$GSVDESM |
|---|---|---|---|
| 0.1 M pH 8.2 carbonate buffer | 30% | 95% | 33% |
| 0.05 M pH 9.0 Tris HCl buffer | 35% | 100% | 20% |

EXAMPLE 7

Production of Anti-Polylysine Tag (K)$_6$SVDESL (SEQ ID NO: 7) Antibodies

The biological material used to obtain the anti-tag antibodies capable of recognizing this tag in the context of a fusion with a recombinant protein is as follows:

the recombinant protein RH24K; this contains, in its amino-terminal part, a polyhistidine tag [MRGS(H)$_6$GSVDESM] (SEQ ID NO: 5), which serves to purify it by chelation with a metal ion, and, in its carboxy-terminal part, a polylysine tag [PG(K)$_6$SVDESL] (SEQ ID NO: 4), which is dedicated to the coupling; this protein is represented by MRGS(H)$_6$GSVDESM-p24-PG(K)$_6$SVDESL the peptide P400, the sequence of which is C(K)$_6$SVDESL (SEQ ID NO: 8), coupled to KLH (P400-KLH).

The biological material used to select the antibodies produced is as follows:

the recombinant protein RH24K the recombinant protein RH24 containing no carboxy-terminal polylysine tag, and represented by MRGS(H)$_6$GSVDESM-p24)

the recombinant protein RH24; this contains neither the carboxy-terminal polylysine tag nor the amino-terminal polyhistidine tag, and is represented by p24.

the peptide P400, the sequence of which is C(K)$_6$SVDESL (SEQ ID NO: 8).

The following two test formats were used to select the monoclonal antibodies:

a sandwich ELISA test, comprising, in the capture phase, an anti-mouse goat antibody, and, in the detection phase, the antigens RH24K or R24 revealed by an anti-24 monoclonal antibody coupled to peroxidase;

an indirect ELISA test, comprising, in the capture phase, the antigens RH24K or R24 or P400, and, in the detection phase, an anti-mouse IgV goat antibody coupled to peroxidase.

BALB/c and A/J mice were immunized according to the following protocol: 3 intra-peritoneal injections with, for the first injection, the protein RH24K, and, for the following two injections, the peptide 400 coupled to KLH. Fusions were carried out and screenings carried out using the sandwich and indirect ELISA tests described above.

80 hybrids were selected according to the following criteria:

recognition of the peptide P400 (C(K)$_6$SVDESL) (SEQ ID NO: 8)

recognition of the protein RH24K (MRGS(H)$_6$GSVDESM-p24-PG(K)$_6$SVDESL)

non-recognition of the protein RH24 (MRGS(H)$_6$GSVDESM-p24)

non-recognition of the protein R24.

These antibodies thus recognize the sequence (K)$_6$SVDESL (SEQ ID NO: 7) fused to a protein, but not the sequence MRGS(H)$_6$GSVDESM (SEQ ID NO: 5) also containing the SVDESL unit, nor the protein p24.

Five of these hybrids were cloned and produced in the form of ascites: these are the antibodies IG2D4, 2G2B3, 2G4A12, 5F12ES and 14E1G7, all of IgG1 k isotype.

Figure 6:
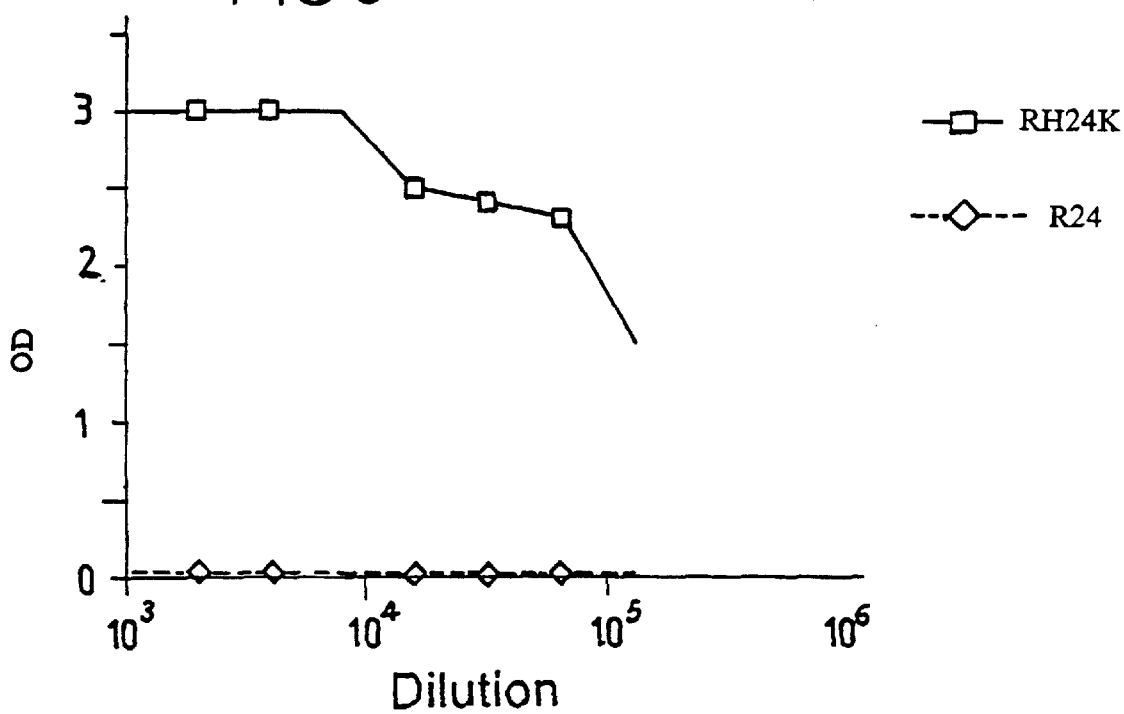
FIG. 6 illustrates the results of a sandwich and indirect ELISA test with the antibody IG2D4, using a graph representing the OD as a function of the antibody titer.
Figure 7:
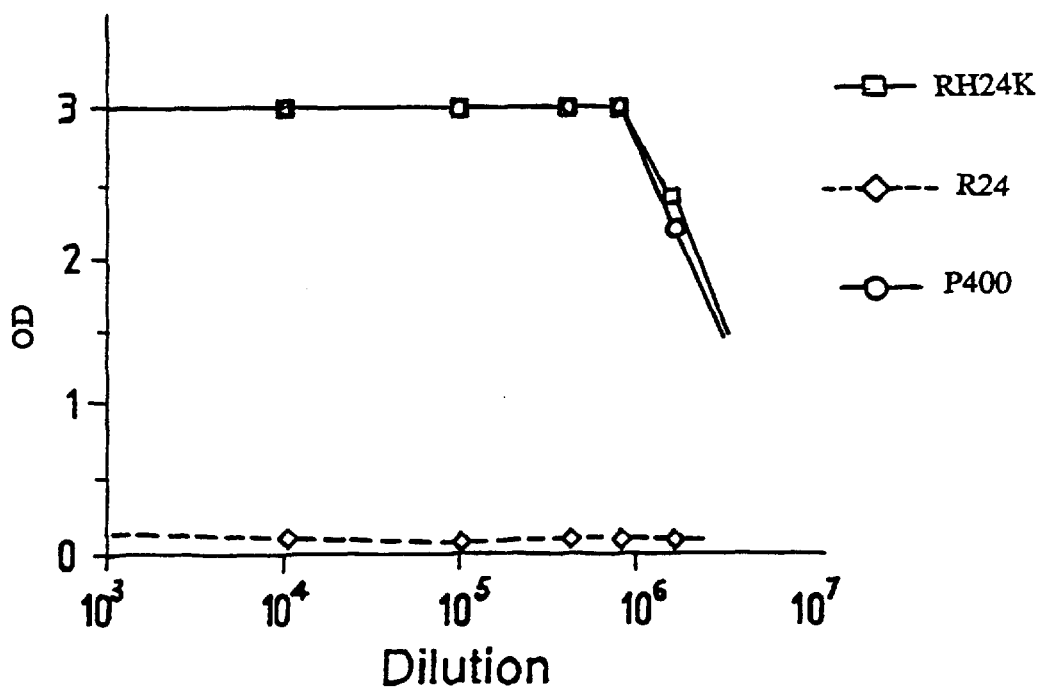
FIG. 7 illustrates the results of an indirect ELISA test with the antibody IG2D4, using a graph representing the OD as a function of the antibody titer.

The results of the sandwich and indirect ELISA tests on the IG2D4 antibodies are illustrated in FIGS. 6 and 7. FIG. 6 illustrates a sandwich ELISA test and represents the OD as a function of the titer (dilution) of the IG2D4 antibody ascite; the recombinant proteins RH24K and R24, constituting the detection phase, are used at a concentration of 0.1 μg/ml. FIG. 7 illustrates an indirect ELISA test and represents the OD as a function of the titer (dilution)(of the IG2D4 antibody ascite; the recombinant proteins RH24K and R24, constituting the capture phase, are used at a concentration of 0.5 μg/ml and the synthetic peptide P400 is used at a concentration of 0.05 μg/ml.

Bibliography (1) Porath J., Carlsson., Olsson., Belfrage J., Nature, 258, 598 (1975)
(2) Porath J., *Trends Anal. Chem.*, 7, 254 (1988)
(3) Cheynet, *Protein Expression and Purification*, 4, 367–372 (1993)

---

What is claimed is:

1. Method for isolating a target biological material contained in a sample, said method comprising:
providing a capture phase;
placing said target biological material in contact with at least the capture phase; and
detecting the target biological material bound to the capture phase,
wherein the capture phase comprises: (a) an organic molecule containing at least one reactive function and (b) at least one protein material capable of recognizing or binding, specifically and directly or indirectly, to the target biological material, said protein material containing a specific site for covalent binding to the reactive function of the organic molecule, which site is comprised of at least one tag comprising at least six contiguous residues selected from the group consisting of lysine and lysine-based residues.

2. Method according to claim 1, wherein the capture phase also comprises a label.

3. Method according to claim 2, wherein the capture phase is a detection phase.

4. Method according to claim 1, wherein a detection phase is also provided, and comprises an organic molecule containing at least one reactive function, at least one protein material capable of recognizing or binding, specifically and directly or indirectly, to the target biological material, and a detectable label, said protein material containing a specific site for covalent binding to the reactive function of the organic molecule.

5. Method according to claim 4, wherein the organic molecule and the protein material in the detection phase are, respectively, identical to and/or different from the organic molecule and the protein material in the capture phase.

6. Method according to claim 4, that the organic molecule in the detection phase is the label.

7. Method according to claim 1, wherein the tag is placed at the N- or C-terminal end of the protein material.

8. Method according to claim 1, wherein the reactive function of the organic molecule is selected from the group consisting of ester, acid, halocarbonyl, sulfhydryl, disulfide, epoxide, haloalkyl and aldehyde functions.

9. Method according to any one of claim 1, wherein the protein material comprises an antigen and the biological material is an antibody that is specifically recognized by said antigen.

10. Method according to claim 1, wherein the protein material comprises an antibody and the biological material is an antigen that is specifically recognized by said antibody.

11. Method according to claim 1, wherein the organic molecule is a particulate or linear polymer.

12. Method according to claim 11, wherein the polymer is selected from the group consisting of polylysine homopolymers, polytyrosine homopolymers, maleic anhydride copolymers, N-vinylpyrrolidone copolymers, natural or synthetic polysaccharides and polynucleotides, and enzymes.

13. Method according to claim 12, wherein the polymer is selected from the group consisting of maleic anhydride/methyl vinyl ether copolymer, N-vinylpyrrolidone/N-acryloxysuccinimide copolymer and poly-6-aminoglucose.

14. Method according to claim 1, wherein the organic molecule is a hapten.

15. Method according to claim 1, wherein the organic molecule is bound to a carrier molecule.

16. Method according to claim 15, wherein the organic molecule is biotin and the carrier molecule is avidin.

17. Capture phase for a target biological material, comprising: (a) an organic molecule containing at least one reactive function and (b) at least one protein material capable of recognizing or of binding, specifically and directly or indirectly, to the target biological material, said protein material containing a specific site for covalent binding to the reactive function of the organic molecule, said site comprising at least one tag comprising at least six contiguous residues selected from the group consisting of lysine and lysine-based residues.

18. Capture phase according to claim 17, wherein the tag is placed at the N- or C-terminal end of the protein material.

19. Capture phase according to claim 17, wherein the reactive function of the organic molecule is selected from the group consisting of ester, acid, halocarbonyl, sulfhydryl, disulfide, epoxide, haloalkyl and aldehyde functions.

20. Reagent for isolating a target biological material, comprising a capture phase according to claim 17.

21. Reagent according to claim 20, wherein the capture phase is bound, directly or indirectly, to a solid support, by passive adsorption or by covalency.

22. Reagent according to claim 20, further comprising a detection phase comprising: (a) a second organic molecule containing at least one reactive function, and (b) at least one protein material capable of recognizing or of binding, specifically and directly or indirectly, to the target biological material, the protein material of said detection phase containing a specific site for covalent binding to the reactive function of the second organic molecule, this site comprising at least one tag comprising at least six contiguous residues selected from the group consisting of lysine and lysine-based residues.

23. Capture phase according to claim 17, wherein the organic molecule is a particulate or linear polymer.

24. Capture phase according to claim 23, wherein the polymer is selected from the group consisting of polylysine homopolymers, polytyrosine homopolymers, maleic anhydride copolymers, N-vinylpyrrolidone copolymers, natural or synthetic polysaccharides and polynucleotides, and enzymes.

25. Capture phase according to claim 24, wherein the polymer is selected from the group consisting of maleic anhydride/methyl vinyl ether copolymer, N-vinylpyrrolidone/N-acryloxysuccinimide copolymer, poly-6-aminoglucose horseradish peroxidase (HRP) and alkaline phosphatase.

26. Capture phase according to claim 17, wherein the organic molecule is a hapten.

27. Detection phase for a target biological material, comprising: (a) an organic molecule containing at least one reactive function, (b) at least one protein material capable of recognizing or of binding, specifically and directly or indirectly, to the target biological material, said protein material containing a specific site for covalent binding to the reactive function of the organic molecule, said site comprising at least one tag comprising at least six contiguous residues selected from the group consisting of lysine and lysine-based residues and (c) a detectable label.

28. Detection phase according to claim 27, characterized in that the organic molecule is the label.

29. Detection phase according to claim 27, wherein the label is selected from the group consisting of an enzyme, a protein, a peptide, an antibody, a hapten a fluorescent compound, a radioactive compound, a chemiluminescent compound, an electron-density component, a magnetic component and analogs thereof.

30. Detection phase according to claim 27, wherein the tag is placed at the N- or C-terminal end of the protein material.

31. Detection phase according to claim 27, wherein the reactive function of the organic molecule is selected from the group consisting of ester, acid, halocarbonyl, sulfhydryl, disulfide, epoxide, haloalkyl and aldehyde functions.

32. Reagent for isolating a target biological material, comprising a detection phase according to claim 27.

33. Reagent according to claim 32, wherein the capture phase is bound, directly or indirectly, to a solid support, by passive adsorption or by covalency.

34. Detection phase according to claim 27, wherein the organic molecule is a particulate or linear polymer.

35. Detection phase according to claim 34, wherein the polymer is selected from the group consisting of polylysine homopolymers, polytyrosine homopolymers, maleic anhydride copolymers, N-vinylpyrrolidone copolymers, natural or synthetic polysaccharides and polynucleotides, and enzymes.

36. Detection phase according to claim 35, wherein the polymer is selected from the group consisting of maleic anhydride/methyl vinyl ether copolymer, N-vinylpyrrolidone/N-acryloxysuccinimide copolymer, poly-6-aminoglucose, horseradish peroxidase (HRP) and alkaline phosphatase.

\* \* \* \* \*